United States Patent
Green et al.

(10) Patent No.: US 7,914,459 B2
(45) Date of Patent: *Mar. 29, 2011

(54) VENTILATOR PATIENT SYNCHRONIZATION

(75) Inventors: Paul Anthony Green, Lindfield (AU); David John Bassin, Coogee (AU)

(73) Assignee: Resmed Limited, Bella Vista, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/765,380

(22) Filed: Apr. 22, 2010

(65) Prior Publication Data

US 2010/0236556 A1    Sep. 23, 2010

Related U.S. Application Data

(63) Continuation of application No. 11/287,746, filed on Nov. 28, 2005, now Pat. No. 7,727,160, which is a continuation of application No. 11/064,592, filed on Feb. 24, 2005, now Pat. No. 6,997,881, which is a continuation of application No. 10/153,343, filed on May 22, 2002, now Pat. No. 6,860,858.

(60) Provisional application No. 60/292,983, filed on May 23, 2001.

(51) Int. Cl.
*A61B 5/08*  (2006.01)
*A61M 16/00*  (2006.01)

(52) U.S. Cl. .................. 600/529; 600/538; 128/204.18; 128/204.21; 128/204.23

(58) Field of Classification Search ................... None
See application file for complete search history.

(56) References Cited

U.S. PATENT DOCUMENTS

| | | |
|---|---|---|
| 4,448,192 A | 5/1984 | Stawitcke et al. |
| 4,915,103 A | 4/1990 | Visveshwara et al. |
| 5,438,980 A | 8/1995 | Phillips |
| 5,513,631 A | 5/1996 | McWilliams |
| 6,230,708 B1 | 5/2001 | Radko |
| 6,318,365 B1 | 11/2001 | Vogele et al. |
| 6,484,719 B1 | 11/2002 | Berthon-Jones |

(Continued)

FOREIGN PATENT DOCUMENTS

EP    0956877    11/1999

(Continued)

OTHER PUBLICATIONS

"Fuzzy Logic", Stanford Encyclopedia of Philosophy, First published Sep. 3, 2002, substantive revision Jul. 23, 2006;Petr Hajek; http://plato.stanford.edu/entries/logic-fuzzy/.

(Continued)

*Primary Examiner* — Charles A Marmor, II
*Assistant Examiner* — Christian Jang
(74) *Attorney, Agent, or Firm* — Gottlieb Rackman & Reisman PC

(57) ABSTRACT

A method and apparatus that provides an expert system for determining respiratory phase during ventilatory support of a subject. Discrete phase states are partitioned and prior probability functions and observed probability functions for each state are defined. The probability functions are based upon relative duration of each state as well as the flow characteristics of each state. These functions are combined to determine phase probabilities for each state using Bayes' theorem. The calculated probabilities for the states may then be compared to determine which state the subject is experiencing. A ventilator may then conform respiratory support in accordance with the most probable phase. To provide a learning feature, the probability functions may be adjusted during use to provide a more subject specific response that accounts for changing respiratory characteristics.

26 Claims, 7 Drawing Sheets

U.S. PATENT DOCUMENTS

| | | |
|---|---|---|
| 6,626,176 B1 | 9/2003 | Madaus et al. |
| 6,629,527 B1 | 10/2003 | Estes et al. |
| 6,860,858 B2 | 3/2005 | Green et al. |
| 6,910,480 B1 | 6/2005 | Berthon-Jones |
| 6,997,881 B2 | 2/2006 | Green et al. |
| 7,727,160 B2 | 6/2010 | Green et al. |

FOREIGN PATENT DOCUMENTS

| | | |
|---|---|---|
| WO | 92/11054 | 7/1992 |
| WO | 93/08857 | 5/1993 |
| WO | 98/12965 | 4/1998 |
| WO | 00/45702 | 8/2000 |
| WO | 01/19440 | 3/2001 |

OTHER PUBLICATIONS

"Bayes' Theorem", Stanford Encyclopedia of Philosophy, First published Jun. 28, 2003, substantive revision Sep. 30, 2003; James Joyce; http://plato.stanford.edu/entries/bayes-theorem/.

Notice of Reasons for Rejection, Japanese Patent Office, Application No. 2002-591073, Apr. 15, 2008.

Notice of Reasons for Rejection, Japanese Patent Office, Application No. 2009-092098, Jul. 14, 2009.

Examination Report, European Patent Office, Application No. 02 771 608.3, Nov. 27, 2009.

Report on Preliminary Examination, Japanese Patent Office, Application No. 2009-092098, Jan. 15, 2010.

Decision of Refusal, Japanese Patent Office, Application No. 2009-092098, Feb. 16, 2010.

VENTILATOR PATIENT SYNCHRONIZATION

This application is a continuation of U.S. patent application Ser. No. 11/287,746 filed Nov. 28, 2005, now U.S. Pat. No. 7,727,160, which is a continuation of U.S. patent application Ser. No. 11/064,592 filed Feb. 24, 2005, now U.S. Pat. No. 6,997,881, which is a continuation of U.S. application Ser. No. 10/153,343 filed May 22, 2002, now U.S. Pat. No. 6,860,858, which claims the priority date of U.S. Provisional Patent Application Ser. No. 60/292,983 filed on May 23, 2001 all of which are hereby incorporated herein by reference in their entirety.

FIELD OF THE INVENTION

This invention relates to methods for synchronizing ventilators with patient respiration. More specifically it relates to methods for estimating the phase in patient respiration using patient flow measurements so that the respiratory support of a ventilator can match the phase of the respiratory cycle of the patient.

BACKGROUND OF THE INVENTION

Mechanical ventilators assisting spontaneously breathing patients strive to synchronize their performance with the patient's efforts. To do this, ventilators typically measure one or more of pressure, volume, flow and time and compare that measure with predetermined thresholds. Some ventilators use respiratory bands around the chest and abdomen of the patient to detect patient effort. The ventilator may then adjust the pressure, volume or flow of air being delivered to the patient in accordance with measure of the patient's efforts. For example, a flow-triggered pressure controlled device may deliver air at one fixed pressure to a patient until the flow crosses a threshold level, whereupon the pressure is changed to another fixed pressure. Depending on their conditions, different patients may experience different levels of discomfort depending upon how quickly and accurately the ventilator tracks the patients' efforts. Simple threshold tests may fail when breaths are irregular, for example, during the presence of coughs, sighs and snores. An improved method and apparatus for ventilator patient synchronization is described in Patent Cooperation Treaty Application PCT/AU97/00631 with publication number WO 98/12965 (Berthon-Jones) where the phase of the patient's respiratory cycle is determined from flow data using fuzzy logic. The specification is hereby included by cross-reference.

Typical apparatus includes a servo 3 controlled blower, comprised of a motor 2 and an impeller 1 connected to a patient interface 5 via an air delivery conduit 6, as shown in FIG. 1. The controller 4 is typically a computer, a processor including memory, or a programmable circuit. One example of patient interface is a nasal mask, others include nose and mouth masks, full face masks and nasal pillows. The pressure in the mask may be measured by a transducer 11 having direct contact with the mask, or alternatively, the transducer may be physically situated in the blower main housing and may estimate the mask pressure using correlations. Flow transducers 10 or other means for measuring flow may also be situated in the mask or in the blower main housing. There are various displays 8 and switches 7 on the blower housing. There is an interface 15 to enable the apparatus to communicate with other devices. Some apparatus include a fixed speed blower whose output is controllably variably vented to atmosphere providing a controlled variable pressure to the patient.

"Expert" systems are known to be used for assisting with medical diagnosis. Such expert systems are typically said to comprise two parts, a "knowledge base" and an "inferencing engine." The knowledge base comprises the set of "expert" information about the system which is used to guide interpretation of the data which has been observed. Sophisticated expert systems may include hundreds, or thousands of pieces of information in the knowledge base. The fuzzy membership rules and weights of Berthon-Jones may be interpreted as the knowledge base. The inferencing engine is the mechanism which combines the knowledge base with the experimental evidence to reach the conclusion. Several different inferencing engines are known, such as those based on fuzzy logic, rule based reasoning and Bayesian likelihoods.

Bayes' theorem[1] quantifies the intuitively appealing proposition that prior knowledge should influence interpretation of experimental observations. One form of Bayes' theorem is:

$$L(H_i | F_j) = \frac{L(H_i) L(F_j | H_i)}{\sum_n L(H_n) L(F_j | H_n)} \quad (1)$$

where L is a likelihood or probability function. Thus, L(H|F) is the likelihood of an hypothesis being true, given observation F, L(H) is the likelihood of the hypothesis being true, and L(F|H) is the likelihood of the observation given the hypothesis being true.

[1] Armitage & Berry (1994) Statistical Methods in Medical Research, 3rd Edition, p 72, Blackwell Science Ltd, Oxford, United Kingdom ISBN 0-632-03695-8

For example, if a physician has observed a particular symptom in a patient, in deciding whether the patient has a particular disease, the physician draws upon the prior evidence of the likelihood that the patient has the particular disease. Several independent observations may be used in conjunction with prior likelihoods to determine the likelihood that an hypothesis is true. The decision may be taken to be the most likely hypothesis.

BRIEF DESCRIPTION OF THE INVENTION

The invention is a method and apparatus for determining phase with probability functions. The method involves partitioning the respiratory cycle into discrete phase states. The states will include inspiration and expiration and preferably include a number of additional states within inspiration and expiration. The probabilities of each phase state are then calculated using probability functions. In the preferred embodiment, the calculation is a function of an "observed probability" determination $L(F_j | H_i)$ and a "prior probability" determination $L(H_i)$. The calculated probabilities $L(H_i | F_j)$ are then compared to determine the actual phase in the patient's respiratory cycle that the patient is experiencing.

Prior probabilities of each particular state may be determined by a function of relative duration, that is, the ratio of each state's duration to the duration of an, entire respiratory cycle. The invention contemplates discrete phase states that may be equivalent in duration or of unequal durations. Such states of different duration may be derived by partitioning the respiratory cycle into sections in relation to a peak flow or differing rates of change of flow. Moreover, calculated probabilities my be adjusted based upon state succession, e.g., increasing the likelihood of the state that follows consecutively from the currently determined state.

The observed probability determination evaluates the likelihood of each state given an observed respiratory characteristic. In the preferred embodiment of the invention, respiratory flow is observed or measured from the patient. In the evaluation, the measure is applied to a probability function that is based upon the predetermined likelihoods between that measure and each potential phase state, for example, the likelihood that a particular range of flow would be associated with a particular state.

The method may also be used to dynamically improve reliability of phase detection by learning the respiratory patterns or characteristics of the patient. By utilizing previously calculated state probabilities to adjust prior probabilities, subsequently calculated state probabilities provide greater patient specific accuracy in phase determination. Moreover, previously recorded breath data can be used to modify the partitioning of phase states or revise the relationship between observed respiratory characteristics and the likelihoods for each state given the observation.

DETAILED DESCRIPTION OF THE INVENTION

Figure 2:
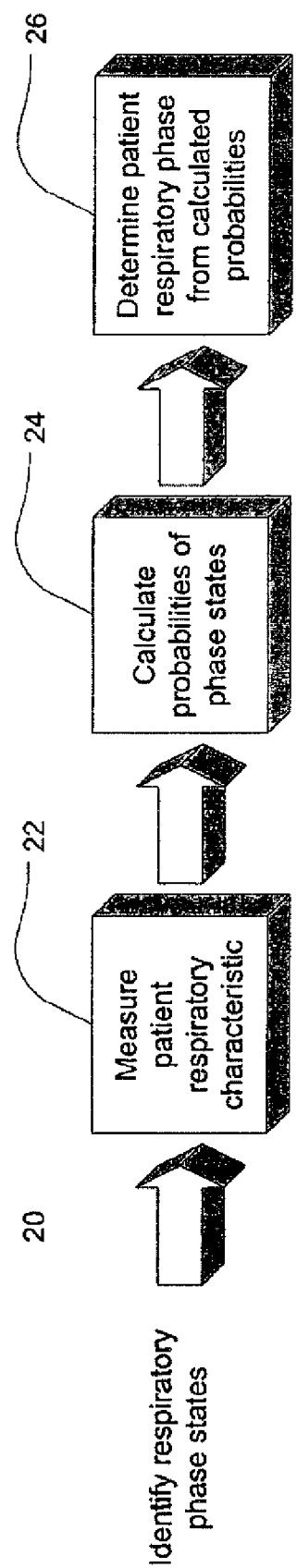
FIG. 2 is a flow chart of steps in a method in accordance with the invention.

The invention provides a method and apparatus for improved ventilator patient synchronization in which the most likely phase is determined on the basis of flow and rate of change of flow information using Bayes' theorem or some similar formula for assessing conditional probability. In an identifying step 20 as shown in FIG. 2, according to the invention, the respiratory cycle is divided or partitioned into a number of distinct states, for example, early inspiration, mid-inspiration, late inspiration, early expiration, mid-expiration, late expiration, pause, sigh and cough. When the method and apparatus according to the invention are being used, flow and pressure observations are made continuously and at each time point in a measuring step 22. In a calculating step 24, probabilities or likelihoods are determined. The likelihood of the phase corresponding to each of the states is determined preferably using Bayes' theorem as shown in equation 1, supra. For example, in a system that distinguishes between six states, six calculations for each distinct state using equation 1 would be made. This evaluation may include an assessment of the prior likelihood of each of the identified states $L(H_i)$. However, these may be determined before use and/or adjusted during use. Likelihoods of the distinct respiratory states occurring given flow and rate of change of flow observations $L(H_i|F_j)$ are also determined. After these evaluations, in a determining step 26, the patient's phase is determined to be the phase which corresponds to the most likely state, e.g. the phase calculation with the highest probability or likelihood.

This information may then be used by the apparatus to adjust the flow, volume or pressure of air being delivered to the patient in order to improve ventilator synchronization.

Figure 3:
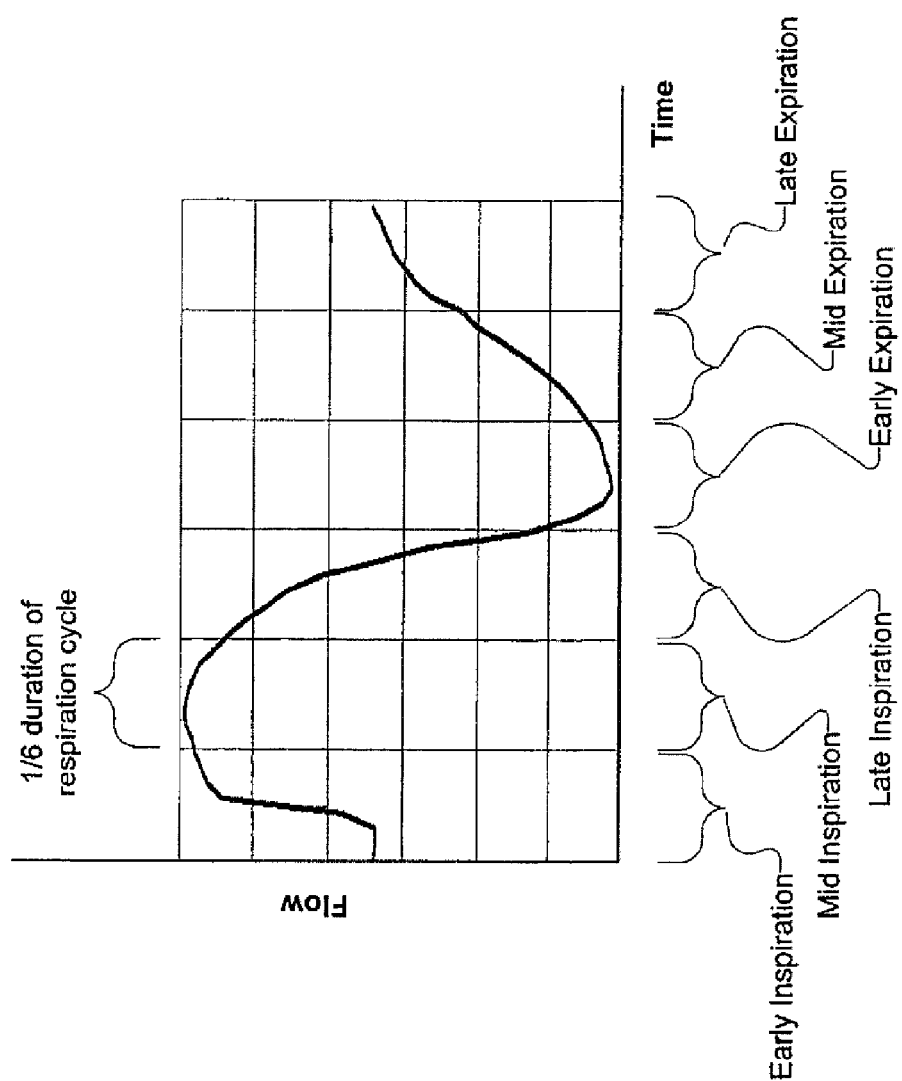
FIG. 3 illustrates phase classification based on equivalent state duration.
Figure 4:
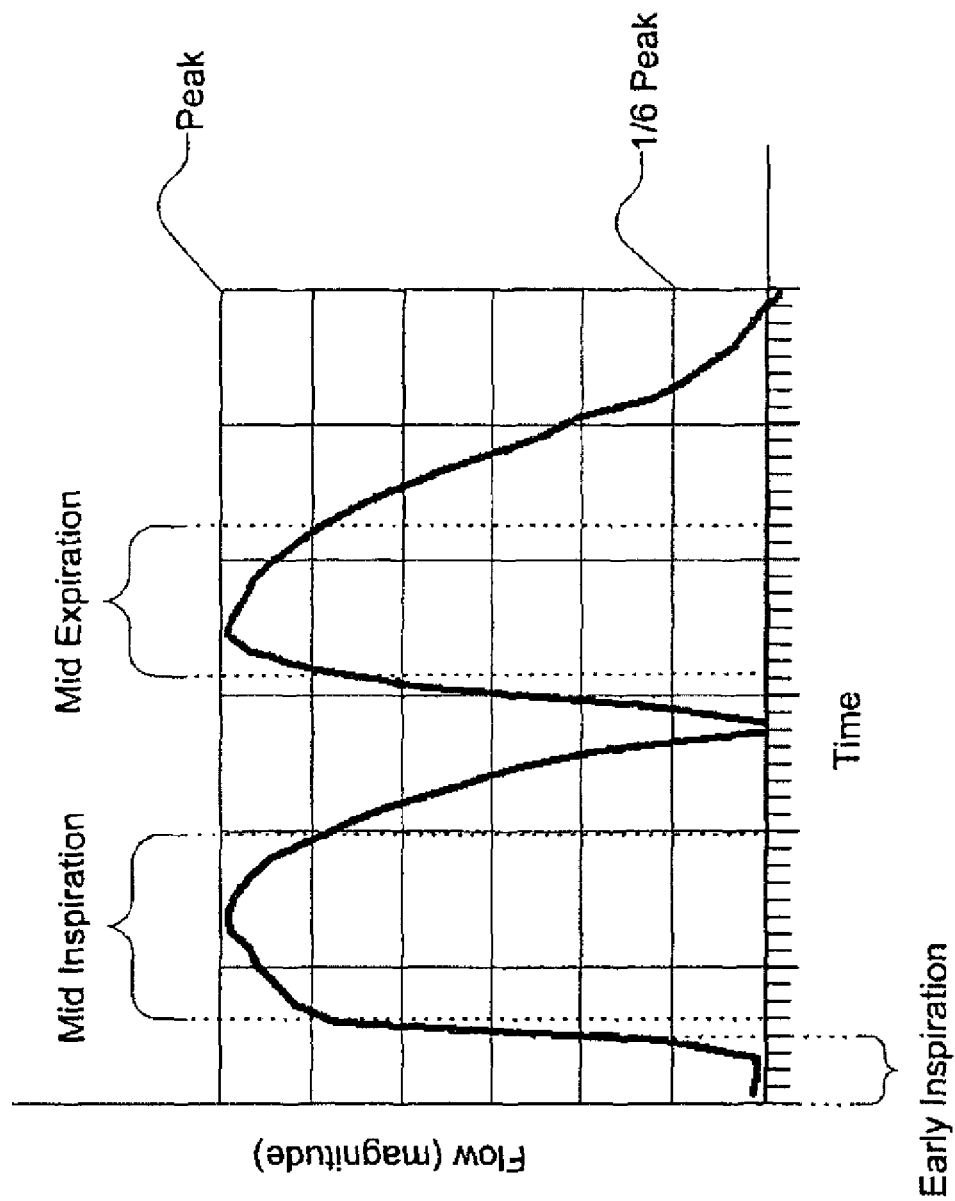
FIG. 4 illustrates phase classification based upon peak flow.

The prior likelihood or prior probability of each state $L(H_i)$ depends upon the definition of the state and its relative duration. Such a determination may be accomplished by a ratio of the duration of the state to the duration of a respiratory cycle. Each state may not necessarily have the same duration. A simple system might divide the respiratory cycle into two states: Inspiration and Expiration. Alternatively, a greater number of states within inspiration or expiration may be classified by the system. If the respiratory cycle led to sinusoidal flow vs. time curves, then it may be appropriate to divide the cycle into equal temporal subsections and assign each subsection as a state in which case, each state may be equally likely a priori. For example, if the duration of a hypothetical respiratory cycle was 6 seconds and the system distinguishes six states, then each state may be one second in duration, the first second being termed "early inspiration", the next second "mid-inspiration" and so on. In this model, the different states may have the same prior likelihoods. Thus, as illustrated in FIG. 3 the likelihood of each state $L(H_i)$ is ⅙ as follows:

$L(H_{early\_inspiration})=1/6$
$L(H_{mid\_inspiration})=1/6$
$L(H_{late\_inspiration})=1/6$
$L(H_{early\_expiration})=1/6$
$L(H_{mid\_expiration})=1/6$
$L(H_{late\_expiration})=1/6$ Increasing the number of states increases the potential accuracy of a system to track changes in respiratory state, however, this comes at an increasing computational cost. It may be computationally more efficient to have states of different duration. In one model of respiration, the states may be chosen on the basis of magnitude of flows, for example early flows from 0 up to ⅙th of the peak flow may be termed "early inspiration". In such a system, for example, as shown in FIG. 4, again based upon a respiration cycle for a typical patient flow. $L(H_{early\_inspiration})$ might be 4/48 where 4 approximates the duration of the state and 48 approximates the duration of the entire cycle, viewed as the intercept of the peak flow range and the flow cycle. Similarly, a mid inspirational state determined from 5/6 to 6/6 of the peak flow might have a likelihood $L(H_{mid\_inspiration})$ equal to 11/48. FIG. 4 also shows a mid expiration state with $L(H_{mid\_expiration})$ equal to 9/48. The remaining states may be determined in similar fashion.

In another model of respiration, the rate of change of flow may be chosen as the basis for dividing the respiratory cycle. Thus, an early inspiration state may be characterized by flow where the rate of change is in a range appropriate to classify the rate of change of respiration in its early stages. Using for example a graph, the duration of a discrete portion of the respiratory cycle in that particular rate of change range divided by the duration of the entire cycle can then yield the prior probability of the particular state $L(H_i)$. An advantage of dividing the respiratory cycle on the basis of rate of change of flow is that those parts of the respiratory cycle where flow changes more rapidly may have more respiratory states assigned to them. In these latter two models, the different states may have different prior likelihoods.

In one form of the invention, the number of states and their definitions may be adaptively refined depending upon the breath data. For example, where the flow rate is changing rapidly, the apparatus according to the invention can determine that it is appropriate to have more states to define that region.

Observation of breath data of patients over several nights leads to the conclusion that a cough is a priori less likely to occur than a breath, since patients breath more often than they cough. It may also be observed that a deep breath is more likely following a number of shallow breaths. Patients are known to pass through a number of different stages during sleep, such as REM sleep. The nature of their breathing can change depending on the different stage of sleep and hence different types of breath are a priori more likely depending on the stage of sleep. To the extent to which a particular patient exhibits characteristic breaths, the system has the capability to learn these characteristics and adjust the prior likelihoods of different states to suit the patient as herein described.

A discrete set of j observations for purposes of determining an observed probability function $L(F_j|H_i)$ may be defined for a flow signal. Similarly, a discrete set of observations of the derivative of flow may be defined. The function may be predefined or changed as a result of changing patient respiratory characteristics. The function may be defined by dividing the range of values for flow or derivative of flow into discrete sub-ranges and then comparing those sub-ranges to each state and assessing probability based upon a typical or previously observed respiratory flow curve's relationship with that sub-range. For example, the flow signal may range from −200 l/min to +200 l/min. This may be divided into the following sub-ranges: −200 to −50, −50 to 0, 0 to 50, 50 to 200 l/min. Noise in the flow signal defines the smallest division into which flow signals may be divided (i.e., there is no point in dividing the total range of flow signals into 1 l/min divisions if the noise level is 2 l/min). The following table, labeled Observation Table 1, gives an example of the likelihoods of the observations being made, given the various hypotheses being true for a system that distinguishes six states. In this example, there is a low likelihood that a large positive flow signal will be observed during the mid expiration phase.

OBSERVATION TABLE 1

| L(F\|H) | Early Inspiration | Mid Inspiration | Late Inspiration | Early Expiration | Mid Expiration | Late Expiration |
|---|---|---|---|---|---|---|
| 200 to 100 (Large positive) | low | high | low | low | low | low |
| 50 to 100 (Medium positive) | medium | medium | medium | low | low | low |
| 0 to 50 (Small positive) | high | low | high | medium | low | medium |
| −50 to 0 (Small negative) | medium | low | medium | high | low | high |
| −100 to −50 (Medium negative) | low | low | low | medium | medium | medium |
| −200 to −100 (Large negative) | low | low | low | low | high | low |

While Observation Table 1 includes the terms "low", "medium" and "high" to describe the likelihoods or probabilities, in actual calculations these terms will be quantified in the ranges of 0-33 percent for low, 33-66 percent for medium and 66-100 percent for high. Moreover, these probabilities need not be limited to three levels. Generally, a change in the boundaries of the states leads to a change in the likelihood of each observation given the hypothesis that the patient is in a given respiratory state is true. Alternatively, the probabilities may be determined from defined continuous likelihood density functions.

Figure 5:
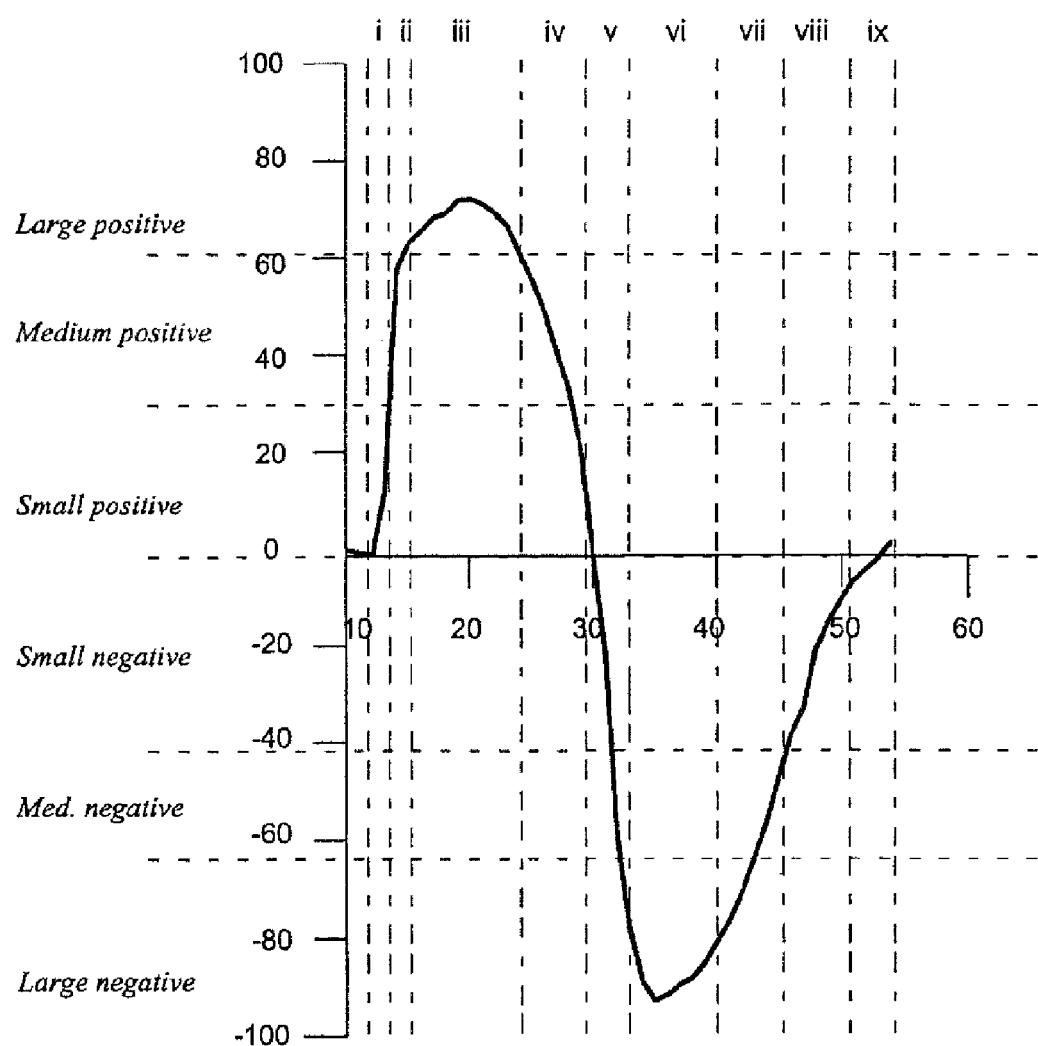
FIG. 5 shows phase classification with a set of observations useful for determining probabilities of the identified states.

FIG. 5 shows sample breath data that is subdivided into 9 states (shown with Roman numerals). Note that states "i", "ii" and "v" are relatively brief compared to states "iii" and "vi". Hence, everything else being equal, states "iii" and "vi" have relatively greater prior likelihoods than states "i", "ii" and "v". The figure also depicts a set of flow observations (large positive to large negative) as the observations relate to the classification of phase states. The observed probabilities $L(F_j|H_i)$ may be determined from this graph. For example, the intercept or observation of a flow in the range of 80-100 (large positive) would suggest a high probability for state iii but low for states i, v, vi, vii, viii, ix. States ii and iv may have low to medium likelihoods as these cases are at the boundary of the large positive observation.

In the following hypothetical example, a calculation of the phase probability or likelihood is demonstrated in accordance with the invention utilizing the simplified six classification system of FIG. 3 in determining L(Hi) and Observation Table 1 for determining L(Fj|Hi). The results are as follows:

Observed Fact F:
Measured flow from flow signal is 150
So $F_j = F_{large\_positive}$
Likelihood of Hypotheses $L(H_i)$:
$L(H_{early\_inspiration}) = 1/6 = 0.167$
$L(H_{mid\_inspiration}) = 1/6 = 0.167$
$L(H_{late\_inspiration}) = 1/6 = 0.167$
$L(H_{early\_expiration}) = 1/6 = 0.167$
$L(H_{mid\_expiration}) = 1/6 = 0.167$
$L(H_{late\_expiration}) = 1/6 = 0.167$
Likelihood of Observation Given Hypothesis $L(H_i|F_j)$
$L(F_{large\_positive}|H_{early\_inspiration}) = 0.25$ (assuming 0.25=low)
$L(F_{large\_positive}|H_{mid\_inspiration}) = 0.75$ (assuming 0.75=high)
$L(F_{large\_positive}|H_{late\_inspiration}) = 0.25$
$L(F_{large\_positive}H_{early\_expiration}) = 0.25$
$L(F_{large\_positive}|H_{mid\_expiration}) = 0.25$
$L(F_{large\_positive}|H_{late\_expiration}) = 0.25$
Bayes' Theorem Calculations:

$$L(H_{early\_inspiration} | F_{large\_positive}) = \frac{0.25 \times 0.167}{0.25 \times 0.167 + 5 \times (0.167 \times 0.25)} = 0.125$$

$$L(H_{mid\_inspiration} | F_{large\_positive}) = \frac{0.75 \times 0.167}{0.25 \times 0.167 + 5 \times (0.167 \times 0.25)} = 0.375$$

$$L(H_{late\_inspiration} | F_{large\_positive}) = \frac{0.25 \times 0.167}{0.25 \times 0.167 + 5 \times (0.167 \times 0.25)} = 0.125$$

$$L(H_{early\_expiration} | F_{large\_positive}) = \frac{0.25 \times 0.167}{0.25 \times 0.167 + 5 \times (0.167 \times 0.25)} = 0.125$$

$$L(H_{mid\_expiration} | F_{large\_positive}) = \frac{0.25 \times 0.167}{0.25 \times 0.167 + 5 \times (0.167 \times 0.25)} = 0.125$$

$$L(H_{late\_expiration} | F_{large\_positive}) = \frac{0.25 \times 0.167}{0.25 \times 0.167 + 5 \times (0.167 \times 0.25)} = 0.125$$

By comparing the calculated probabilities $L(H_i|F_j)$ to find the most probable phase, it is apparent that in this simplified example the phase is early inspiration. With this determination, a system providing ventilatory support may automatically adjust the support to accommodate the patient's phase, for example, by adjusting a pressure gain associated with the particular state of the determined phase. Moreover, the probability for the phase $L(H_i)$ may be modified after calculations to improve subsequent determinations by adjusting $L(H_i)$ to equal or approach the determined phase likelihoods $L(H_i|F_j)$ by a function of $L(H_i|F_j)$. Moreover, the likelihoods of each of the observations $L(F_j|H_i)$ may be updated based upon recorded breath data representing a prior respiratory cycle or some average of the prior respiratory cycles.

Figure 1:
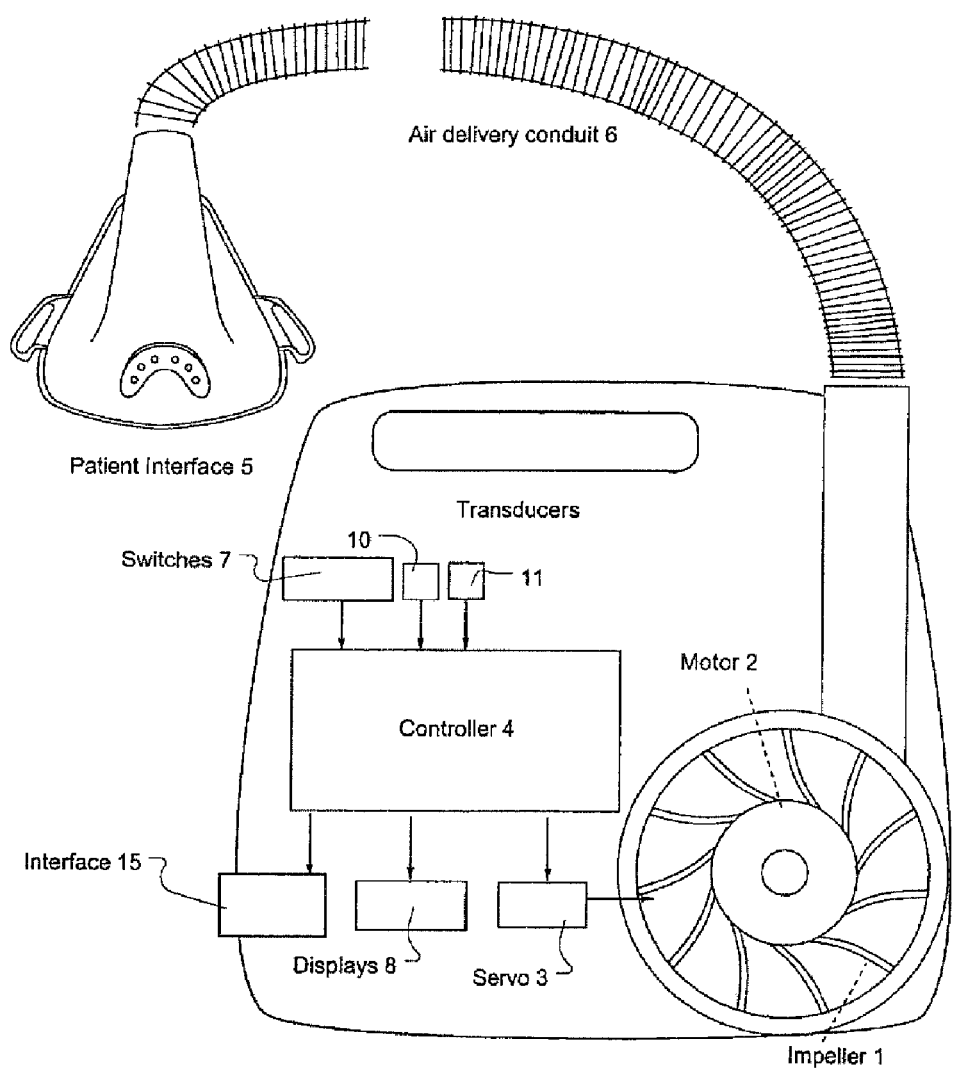
FIG. 1 depicts a prior art ventilator apparatus suitable for use with the invention.

In accordance with the invention, a processor of a ventilator apparatus like that illustrated in FIG. 1 is programmed with an algorithm that accomplishes the following preferred method:

I. Repeat the following with a first time constant:
(a) Update the prior likelihood for each state $L(H_1)$
(b) Update the likelihood of each observation, given each state $L(F_j|H_i)$ II. Repeat the following with a second time constant:
(a) Measure flow, determine rate of change of flow
(b) Calculate the likelihood $L(H_i|F_j)$ for each state using Bayes' theorem.
(c) Phase is determined to be the most likely state.

The first time constant may be in the order of several typical breaths, for example 10 to 15 s. The second time constant is shorter, for example, 1/20th of the duration of a typical breath, or several hundred milliseconds.

In one form, the apparatus according to the invention provides a training period when the patient is allowed to wear the mask in a relaxed environment. The flow and pressure in the mask are monitored and the device has the opportunity to learn some of the characteristics of the patient's respiratory patterns. During this period adjustments to the functions for likelihoods $P(H_i)$ and $P(F_j|H_i)$ for each state of the system can be made using $L(H_i|F_j)$ and observed breath data and/or the partitioning of phase states may change. The respiratory characteristics of the patient will change when the patient falls asleep, however, the apparatus can monitor the transition to the sleep state and estimate probable parameters for the sleep state.

Figure 6:
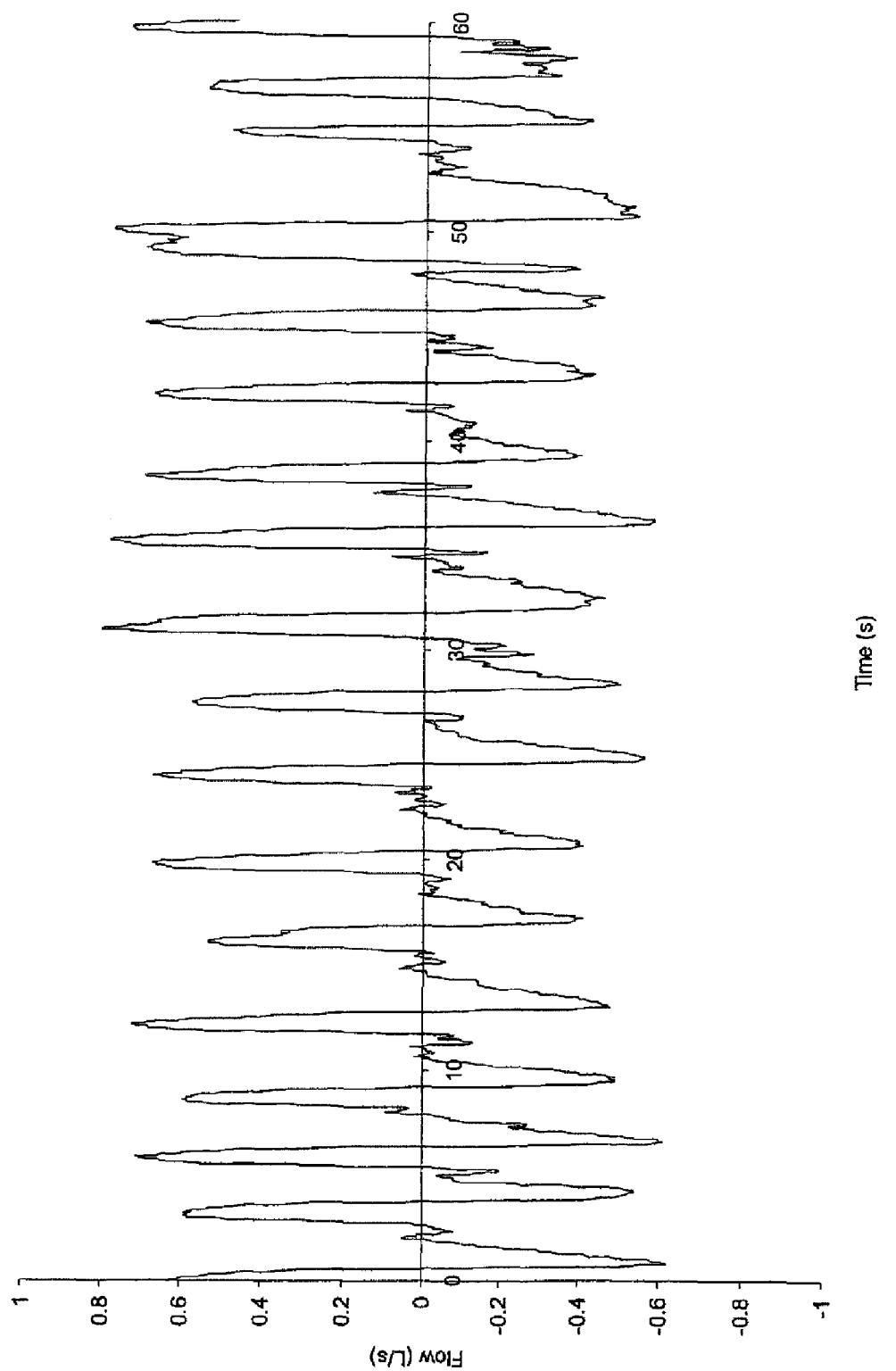
FIG. 6 shows flow versus time data for a person over a period of 1 minute.
Figure 7:
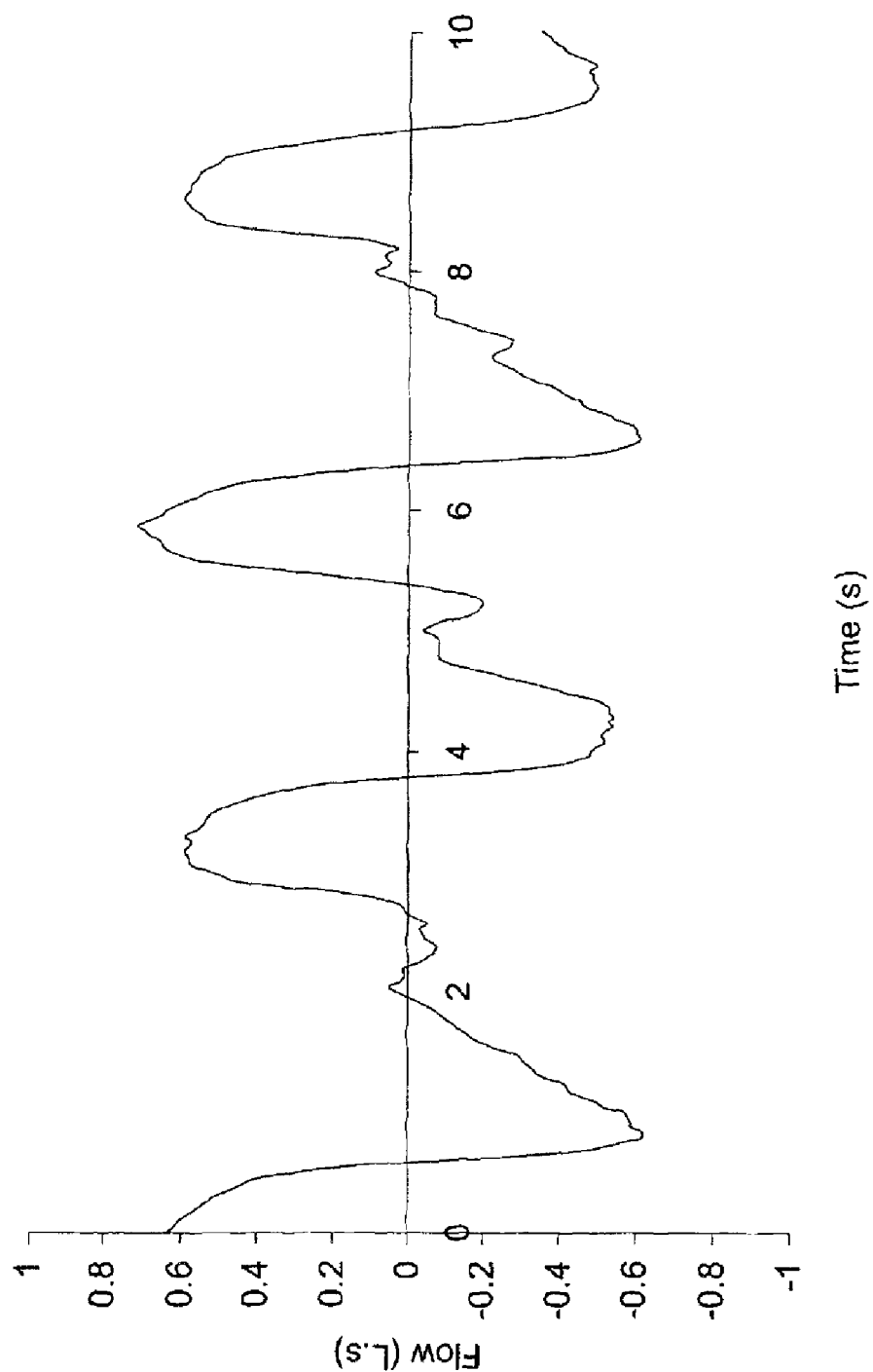
FIG. 7 shows flow versus time data for a person over a period of 10 seconds.

While patient respiratory flow can be modeled as being generally sinusoidal, in reality, the data are more complicated. For example, FIGS. 6 and 7 show flow data from a person over periods of 1 minute and 10 seconds respectively. The data can be additionally complicated with the presence of noise, artefact, drift, sighs, coughs and other events. During the presence of flows of small absolute value, the effect of heart beat (the so-called "cardiogenic effect") on flow data can be identified. These complications, which may be termed "non-idealities", mean that a simple automatic system may incorrectly decide phase.

For example, with reference to FIG. 7, a system based purely on threshold values might conclude that the patient had moved to the inspiratory phase at approximately 2 seconds, and then a short while later, for example a hundred milliseconds, gone to the expiratory phase, and then switched back to the inspiratory phase once again. In a simplified automatic system, such a breath may complicate calculations of the length of a respiratory cycle and the volume of air inhaled or exhaled. Hence there is a need for a method and apparatus which can accurately determine the phase of a respiratory cycle of a patient from complex flow data. There is a need for a method and apparatus which is less likely to be confused by non-ideal flow when determining the phase of the patient.

One approach to solving the problem of dealing with non-idealities in flow data is to smooth the data, for example by low-pass filtering the data in the measuring step 22. A low pass filter may be characterized by the time constant of the filter. A small time constant may mean that the amount of smoothing is small, but the system can respond more quickly. A larger time constant may mean that the data is smoother, but that the system does not respond as quickly. A very large time constant—essentially a long term average—may remove all phase information. Hence there is a need to choose an appropriate time constant if the data are to be smoothed. Furthermore, there may be an advantage in a system that learns from the flow data of the patient what an appropriate time constant may be. Such a system can dynamically update the time constant if necessary.

Determining the derivative of noisy data can be particularly problematic. An algorithm for calculating a derivative may give very different results depending on the period over which the data is analyzed. For example with reference to FIG. 7, an algorithm which calculated the derivative of data over the region from 2 seconds to 2.1 seconds may give a negative value, while an algorithm which calculated the derivative over the region from 2 seconds to 2.5 seconds may give a near zero value. A turning point is a part of a curve where the slope of the curve changes between positive and negative, that is, the second derivative is zero. Similarly, the data at the end of a respiratory cycle (that is, after exhalation and before inhalation) can be particularly non-ideal because of the presence of cardiogenic flow. As a result, the calculations for determining the derivative of flow at the end of a respiratory cycle can be problematic and error prone.

To overcome this problem, an algorithm for determining phase in accordance with the invention may first determine whether the patient is likely to be near the end of a respiratory cycle (for example, if the absolute value of a flow datum is, small, hence distinguishing from peak inspiration and peak exhalation). If the patient is likely to be near the end of a respiratory cycle, then a different time constant may be applied to the smoothing of data for the purposes of calculating a derivative. In a preferred embodiment, the time constant will be longer in the region near the end of the respiratory flow curve than at other regions, such as early to late inspiration and early to late expiration. Furthermore, in an algorithm in accordance with the invention, the effect of the derivative in determining the phase of the patient's respiratory cycle is given less weight in the region where derivative calculations are likely to be error prone, such as one or more of the following: the end of the respiratory cycle, peak inspiration, and peak expiration. Furthermore, in an algorithm in accordance with an embodiment of the invention, an a priori likelihood function for the derivative of flow in the end of the respiratory cycle has a maximum at a low or zero value of flow and a minimum at large values of the derivative. In other words, in an algorithm in accordance with an embodiment of the invention, in this region, a low value of the derivative has a higher likelihood than a high value of the derivative.

In a preferred embodiment of the invention, 12 bit flow data are collected at 50 Hz. The data are low pass filtered with a time constant of 160 ms.

As previously described, in a system in which phase is divided into several states, an algorithm in accordance with an embodiment of the invention may determine that the patient is in one of those states, for example the state with the largest likelihood or probability. Alternatively the algorithm may determine that phase is part way between two adjacent states with high likelihoods. The algorithm may determine that the phase is closer to the one of the two states with the highest likelihood, for example, by weighting in accordance with the relative size of the likelihoods. Hence if one state is 95% likely and another is 70% likely, the phase will be determined to be closer to the state which is 95% likely. In this regard, phase may be determined as a continuous variable. For example, phase may vary from 0 to 1 depending on the state determined or depending on the proximity between two most likely states. Alternatively or additionally, phase may be represented using polar coordinates and vary from 0 to 360 degrees, or 0 to 2 pi radians.

To illustrate such a determination, phase may be calculated as a continuous variable $\phi$. One way to estimate this from a series of posterior probabilities $P_i$ of N states $S_i$ is to associate each state with a standard phase $\phi_{s,i}$ and weighting factor $W_i$ then calculate $\phi$ as $$\phi = \sum_{i=1}^{N} P_i W_i \phi_{s,i}$$

Another approach is to use the formulation of Bayes theorem in terms of continuous random variables, which yields the following posterior density function (assuming here that the information available about the patient is the instantaneous respiratory flow q), $$P_{\Phi|Q}(\phi,q)$$

and the estimate of $\phi$ is that value which maximizes the posterior density given the observed value q of patient flow (this may be a local or global maximum). In practice, the prior and conditional densities which are used to calculate the posterior density may be estimated from discrete data, possibly by using continuous interpolating functions such as piecewise linear or cubic spline functions. The posterior density function may then be calculated (possibly piecewise) analytically or via numerical methods, yielding a posterior density function which may thus be a continuous function of $\phi$ and q. If the posterior density is a continuous function, it follows that since flow q is a continuous function of time then the estimated phase $\phi$ is a continuous function of time.

Such a continuous phase variable may then be used to adjust ventilator support pressure. For example, if the pressure delivered to the patient is based on a continuous function $\Pi$ of phase, $$P = P_{min} + A\Pi(\phi)$$

where $P_{min}$ and A are constants or slowly varying quantities, then an important consequence of the phase being a continuous function of time is that the pressure is a continuous function of time, which may be desirable for example in order to avoid the discomfort which may be associated with sudden changes in pressure delivered to the airway.

Of course, as the number of discrete states increases, the representation of phase may be regarded as a continuous, rather than discrete function. This may alleviate a need for the additional calculation of a continuous phase variable from the determined phase states. In this regard, although six and nine states have been identified in prior embodiments, by way of example, phase may be divided into as many as 128 or 256 states.

In an algorithm in accordance with an embodiment of the invention, phase determinations may be enhanced by other phase related likelihoods. For example, consecutive phase states are more likely than non-consecutive phases. Thus, a phase determination may be based in part upon the likelihood that the current state is the next consecutive state from a previously determined state. To illustrate such a process, suppose that it has been determined that the current phase state is early inspiration. If the next phase state is mid-inspiration, then mid-inspiration is a priori more likely than a non-consecutive state, such as late inspiration or an expiratory state. Hence as phase progresses through the cycle, a priori likelihoods are adjusted in accordance with their consecutive status, for example by increasing the calculated probability of the next consecutive state. This is not to say that an algorithm in accordance with an embodiment of the invention cannot make a determination that a non-consecutive state will follow the current state, but simply that it is less likely to make such a determination. Hence in an algorithm in accordance with an embodiment of the invention, phase "cycling"—where the algorithm flips back and forward between two states—is less likely.

Although the invention has been described with reference to particular embodiments, it is to be understood that these embodiments are merely illustrative of the application of the principles of the invention. Thus, it is to be understood that numerous modifications may be made in the illustrative embodiments of the invention and other arrangements may be devised without departing from the spirit and scope of the invention.

The invention claimed is:

1. An apparatus for delivering ventilatory support to a subject synchronized to the subject's respiratory phase, comprising:
    a means for providing a controlled supply of breathable gas to a subject's airway;
    a means for generating an air flow signal representative of the subject's respiration; and
    a processor to determine a phase of the subject's respiratory cycle and to control the supply of breathable gas delivered to the subject's airway;
    wherein said processor determines a phase in the subject's respiratory cycle by (a) designating a plurality of phase states within said subject's respiratory cycle, each phase including one or more phase states; (b) calculating a measure of the subject's respiration from said air flow signal; (c) determining probabilities for said subject being in each of said phase states based on said measure of respiration; and (d) identifying a phase in the subject's respiratory cycle from the determined probabilities of said subject's respiratory cycle being in each of said phase states; and
    said processor causes the delivery of a supply of breathable gas synchronized with the determined phase of the subject's respiratory cycle.

2. The apparatus of claim 1 wherein said means for providing a controlled supply of breathable gas includes a ventilator and said means for generating an air flow signal representative of the subject's respiration includes a transducer.

3. The apparatus of claim 1 wherein said probabilities are determined based on the ratio of each phase state's duration to the duration of an entire respiratory cycle.

4. The apparatus of claim 1 wherein said probabilities are determined based on the ratio of each phase state's duration to the duration of an entire respiratory cycle and also as a function of previously determined probabilities.

5. The apparatus of claim 1 wherein said probabilities are determined using a comparing function that relates said plurality of phase states to sub-ranges selected from a range of measures of a respiratory cycle.

6. The apparatus of claim 1 wherein said comparing function changes as a result of changing respiratory cycles of the subject.

7. The apparatus of claim 1 wherein said processor identifies a phase by additionally comparing determined probabilities to identify a determined probability that is more probable than other determined probabilities.

8. The apparatus of claim 1 wherein said designating a plurality of phase states involves partitioning a respiration cycle in relation to a peak flow.

9. The apparatus of claim 1 wherein said designating a plurality of phase states is repeated to adjust said phase states to account for the subject's changing respiratory characteristics as assessed by a measure of respiration over time.

10. The apparatus of claim 9 wherein said calculating a measure of the subject's respiration includes smoothing data and performing a low pass filtering operation on said data from said air flow signal.

11. The apparatus of claim 1 wherein said determining probabilities involves an evaluation of prior probabilities and observed probabilities as a function of Bayes' theorem.

12. The apparatus of claim 1 wherein said determining probabilities includes adjusting a probability based upon state succession.

13. The apparatus of claim 1 wherein said designating a phase involves calculating a continuous phase variable from said probabilities.

14. A method for delivering ventilatory support to a subject at a pressure synchronized with the subject's respiratory phase using a processor, comprising the steps of:
generating, using the processor, an air flow signal representing said subject's air flow;
calculating, using the processor, a measure of the subject's respiration from said air flow signal;
designating, using the processor, a plurality of phase states within the subject's respiratory cycle, wherein each phase is comprised of one or more phase states;
determining, using the processor, probabilities for said subject's respiratory cycle being in each of said phase states based on the measure of the subject's respiration;
identifying, using the processor, a phase in the subject's respiratory cycle from the calculated probabilities of said phase states; and
delivering a supply of breathable gas using a ventilator at a pressure synchronized with the determined phase of the subject's respiratory cycle.

15. The method of claim 14 wherein said air flow signal is generated using a transducer.

16. The method of claim 14 wherein said probabilities are determined based on the ratio of each phase state's duration to the duration of an entire respiratory cycle.

17. The method of claim 14 wherein said probabilities are determined based on the ratio of each phase state's duration to the duration of an entire respiratory cycle and also as a function of previously calculated probabilities.

18. The method of claim 14 wherein said probabilities are determined using a comparing function that relates said plurality of phase states to sub-ranges selected from a range of measures of a respiratory cycle.

19. The apparatus of claim 18 wherein said comparing function changes as a result of changing respiratory cycles of the subject.

20. The method of claim 14 wherein a phase is identified by additionally comparing determined probabilities for one that is more probable than other determined probabilities.

21. The method of claim 14 wherein said designating a plurality of phase states involves partitioning a respiration cycle in relation to a peak flow.

22. The method of claim 14 wherein said designating a plurality of phase states is repeated to adjust said phase states to account for the subject's changing respiratory characteristics as assessed by a measure of respiration over time.

23. The apparatus of claim 22 wherein calculating a measure of the subject's respiration includes smoothing data and performing a low pass filtering operation on said data from said respiration.

24. The method of claim 14 wherein said determining probabilities involves an evaluation of prior probabilities and observed probabilities as a function of Bayes' theorem.

25. The method of claim 14 wherein said determining probabilities includes adjusting a probability based upon state succession.

26. The method of claim 14 wherein said identifying a phase involves calculating a continuous phase variable from said determined probabilities.

* * * * *